United States Patent
Sacristan

(10) Patent No.: US 7,074,176 B2
(45) Date of Patent: Jul. 11, 2006

(54) AIR-PRESSURE POWERED DRIVER FOR PNEUMATIC VENTRICULAR ASSIST DEVICES

(75) Inventor: Emilio Sacristan, Santa Ursula Xitla (MX)

(73) Assignee: Innovamedica S.A. de C.V. (MX)

( * ) Notice: Subject to any disclaimer, the term of this patent is extended or adjusted under 35 U.S.C. 154(b) by 190 days.

(21) Appl. No.: 10/846,983

(22) Filed: May 13, 2004

(65) Prior Publication Data

US 2004/0230089 A1    Nov. 18, 2004

Related U.S. Application Data

(60) Provisional application No. 60/470,711, filed on May 15, 2003.

(51) Int. Cl.
*A61N 1/362*    (2006.01)
(52) U.S. Cl. .................................. 600/17; 623/3.11
(58) Field of Classification Search ............. 600/16–18; 623/3.1, 3.16, 3.28; 417/383–385, 388
See application file for complete search history.

(56) References Cited

U.S. PATENT DOCUMENTS

| | | | |
|---|---|---|---|
| 3,208,448 A | 9/1965 | Woodward | |
| 3,266,487 A | 8/1966 | Watkins et al. | |
| 3,425,064 A | 2/1969 | Carnevale et al. | |
| 3,720,199 A | * | 3/1973 | Rishton et al. ........... 600/18 |
| 4,465,063 A | 8/1984 | Nielsen et al. | |
| 4,536,893 A | 8/1985 | Parravicini | |
| 4,634,430 A | 1/1987 | Polaschegg | |
| 4,756,302 A | 7/1988 | Portner et al. | |
| 4,969,866 A | 11/1990 | Inagaki | |
| 5,397,349 A | 3/1995 | Kolff et al. | |
| 5,707,336 A | 1/1998 | Rubin | |
| 5,713,954 A | 2/1998 | Rosenberg et al. | |
| 5,738,627 A | 4/1998 | Kovacs et al. | |
| 5,749,839 A | 5/1998 | Kovacs | |
| 5,858,962 A | 1/1999 | Blackburn et al. | |
| 5,902,229 A | 5/1999 | Tsitlik et al. | |
| 5,913,814 A | 6/1999 | Zantos | |
| 5,971,910 A | 10/1999 | Tsitlik et al. | |
| 6,098,405 A | 8/2000 | Miyata et al. | |
| 6,120,431 A | 9/2000 | Magovern et al. | |
| 6,206,820 B1 | 3/2001 | Kazi et al. | |
| 6,238,334 B1 | 5/2001 | Easterbrook, III et al. | |
| 6,254,525 B1 | 7/2001 | Reinhardt et al. | |
| 6,398,715 B1 | 6/2002 | Magovern et al. | |
| 6,406,422 B1 | 6/2002 | Landesberg | |
| 6,508,756 B1 | 1/2003 | Kung et al. | |
| 6,511,412 B1 | 1/2003 | Freed et al. | |
| 6,511,413 B1 | 1/2003 | Landesberg | |
| 6,540,659 B1 | 4/2003 | Milbocker | |
| 6,547,534 B1 | 4/2003 | Sakamoto et al. | |
| 6,572,534 B1 | 6/2003 | Milbocker et al. | |

\* cited by examiner

*Primary Examiner*—Robert E. Pezzuto
*Assistant Examiner*—Jessica L. Reidel
(74) *Attorney, Agent, or Firm*—Holland & Bonzagni, P.C.; Donald S. Holland, Esq.

(57) ABSTRACT

A driver for a pneumatic ventricular assist device (VAD) is powered by pressurized air, oxygen or any other gas commonly available in hospital rooms, intensive care units and operating rooms. The driver can provide both blood-ejecting pressure (systole) and blood-filling vacuum (diastole) to the VAD. The driver is controlled by a computer/digital controller by means of pressure and volume sensors, and electromechanical valves. Ventricular pumping is performed by a single spring-loaded piston or bellows. The computer can actively regulate maximum systolic ventricular pressure, maximum diastolic vacuum, cycling rate and/or ejection volume (depending on the operating mode). The driver is also capable of automatically and periodically venting the drive line to eliminate condensation and foul air. The absence of a motor or electrical pump make the device small, reliable, easy to handle, and less expensive.

14 Claims, 5 Drawing Sheets

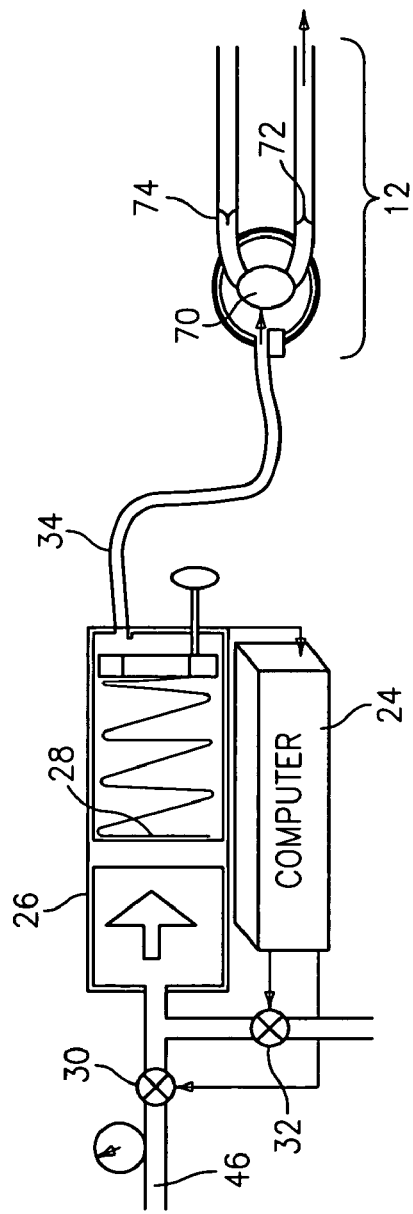
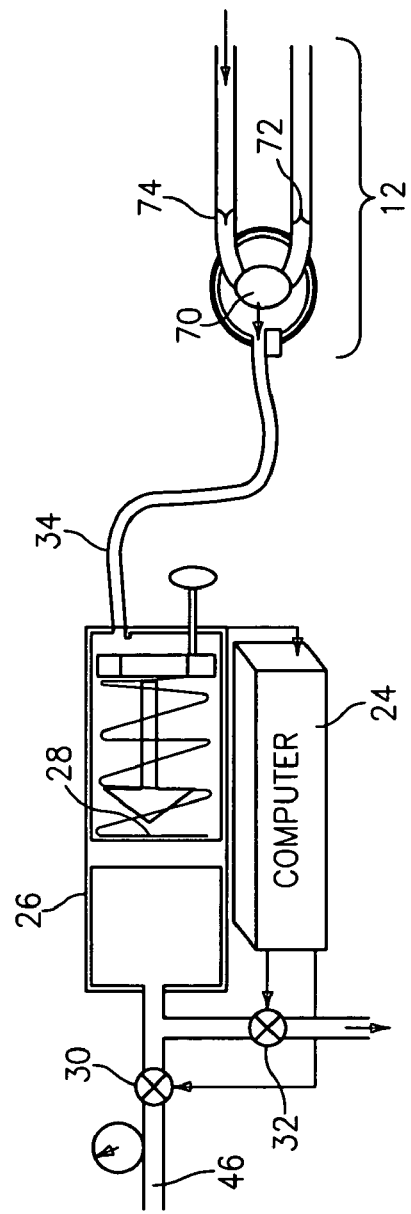
FIG. 2A
FIG. 2B

AIR-PRESSURE POWERED DRIVER FOR PNEUMATIC VENTRICULAR ASSIST DEVICES

This application claims priority from a Provisional Application, Ser. No. 60/470,711, filed May 15, 2003.

FIELD OF THE INVENTION

The present invention relates to medical equipment, and, more particularly, to machines for powering pneumatic ventricular assist devices.

BACKGROUND

Ventricular assist devices ("VAD") are used to help supplement the heart's pumping action both during and after certain kinds of surgery, in situations where a complete cardiopulmonary bypass (using a heart-lung machine) is neither needed nor advisable in light of the serious side effects associated therewith. Ventricular assist devices typically comprise a pair of cannulae or other tubing and some sort of pump operably connected to the cannulae. In use, the cannulae are attached to either the left side of the heart (a left ventricular assist device) or to the right side of the heart (a right ventricular assist device) "in parallel," i.e., the pump supplements the heart's pumping action but does not completely bypass it, and the pump is activated. Alternatively, a pump may be directly implanted into the body.

Originally, ventricular assist devices were air powered, wherein fluctuating air pressure, provided by a simple mechanical air pump machine, was applied to a bladder-like sac. The bladder had input and output valves, so that blood would enter the bladder through the input valve when the pressure on the bladder was low, and exit the bladder through the output valve when the pressure on the bladder was high. Unfortunately, these pneumatic ventricular assist devices were complicated, and used expensive mechanical valves that were prone to failure, subject to "clogging," and that caused blood trauma or damage because of hard, metal edges and the like.

To overcome these problems, smaller, more reliable ventricular assist devices have been in use and/or development. These include axial flow pumps for temporary insertion directly into the heart, and peristaltic or centrifugal pumps. The former are based on the Archymides' Principle, where a rod with helical blades is rotated inside a tube to displace liquid. In use, a catheter-mounted, miniature axial flow pump is appropriately positioned inside the heart, and is caused to operate via some sort of external magnetic drive or other appropriate mechanism. With high enough RPM's, a significant amount of blood can be pumped. In the case of peristaltic pumps, blood is moved by the action of a rapidly rotating impeller (spinning cone or the like), which causes the blood to accelerate out an exit. Both of these categories of ventricular assist devices are generally reliable and implantable, but are very expensive, not particularly durable, and are not useful in situations where a patient needs a true pulsating blood supply. Specifically, axial and peristaltic pumps are typically left on in a continuous operation mode, where a steady stream of blood is supplied on a continuous basis, as opposed to the natural rhythm of the heart, which acts on a periodic, pulse-producing basis. In addition, such pumps are still largely in the developmental or trial phase.

Because of the inherent performance limitations of these ventricular assist devices, pneumatic devices would seem to be a good choice for providing pulsing pulmonary augmentation. However, as mentioned above, pneumatic ventricular assist devices are prone to failure and can cause blood damage and clotting. Moreover, the driver units for operating the pneumatic ventricular assist devices are motor-based (therefore, generally mechanically unreliable), and can only offer a simple cyclical pressure mode of operation, i.e., a repeating minimum and maximum pressure applied to the VAD bladder, which cannot be adjusted for particular patient conditions.

Accordingly, a primary object of the present invention is to provide a driver for pneumatic ventricular assist devices that is more reliable, that has no electrical pump or motor, and that provides a greater degree of operational flexibility and customization.

SUMMARY

A gas powered driver or driver means for a pneumatic ventricular assist device (VAD) is powered by pressurized air, oxygen or any other gas commonly available in hospital rooms, intensive care units and operating rooms. The driver can provide both blood-ejecting pressure (systole) and blood-filling vacuum (diastole) to the VAD. The driver is controlled by a computer/digital controller by means of pressure and volume sensors, and electromechanical, computer-controlled valves. Ventricular pumping is performed by a single spring-loaded piston or bellows inside a pump cylinder. The computer can actively regulate maximum systolic ventricular pressure, maximum diastolic vacuum, cycling rate and/or ejection volume (depending on the operating mode). The driver is also capable of automatically and periodically venting the drive line to eliminate condensation and foul air. The absence of a motor or electrical pump make the device small, reliable, easy to handle, and inexpensive.

BRIEF DESCRIPTION OF THE DRAWINGS

These and other features, aspects, and advantages of the present invention will become better understood with respect to the following description, appended claims, and accompanying drawings, in which:

FIGS. 2A & 2B are schematic diagrams of a portion of the air-pressure powered driver in operation.

DETAILED DESCRIPTION

Figure 1:
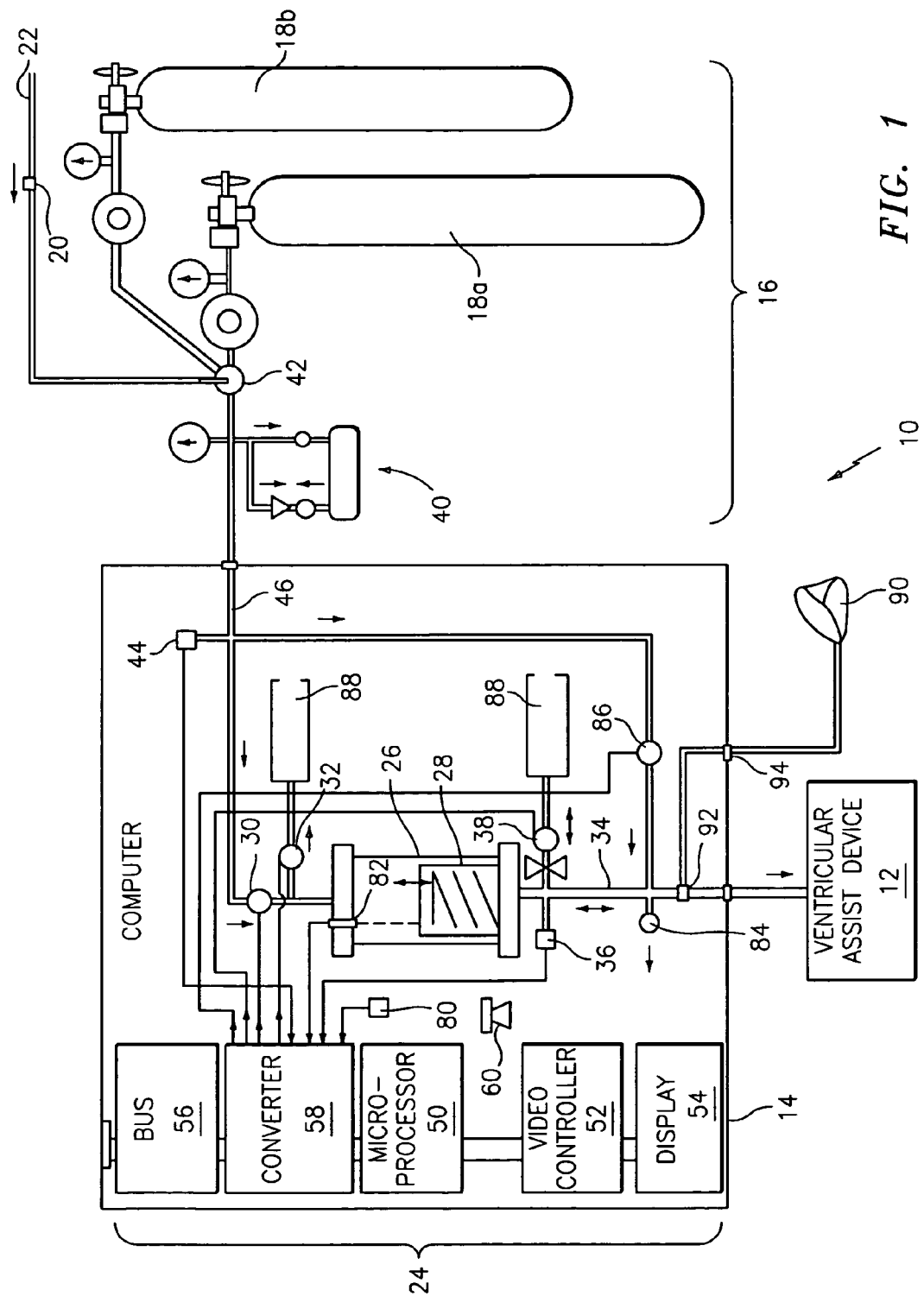
FIG. 1 is a schematic diagram of an air-pressure powered driver for pneumatic ventricular assist devices, according to the present invention.

With reference to FIG. 1, a preferred embodiment of a gas pressure powered driver or driver means 10 for driving a pneumatic ventricular assist device 12 (VAD) includes a console unit 14 and a pressurized air/gas unit 16, which includes one or more backup tanks (e.g., 18a, 18b) of pressurized gas (preferably air) and a gas input connector 20 that attaches to a facility-wide pressurized air line 22. The console unit 14 includes a computer or other electronic controller 24, a pump cylinder or positive-displacement pump (i.e., piston or bellows) 26 with a sealed, gas moveable member 28 (i.e., piston or bellows), an inlet pressure valve 30, and a cylinder venting valve 32, both of which are attached to the pressurized air source 16 and the source (or input) end of the pump cylinder 26. A tubular outlet "driveline" (i.e., a line that can be pressurized to drive a device) 34 is connected to the discharge or output of the pump 26. The driveline, in turn, is attached to the ventricular assist device 12. In use, at the beginning of a cycle, the computer 24 opens the inlet pressure valve 30 to compress the bellows and spring 28 and raise the systolic pressure in the VAD 12 (active systole). Once the maximum desired driveline pressure is achieved, as measured by a driveline pressure sensor 36 electrically connected to the computer 24, the inlet pressure valve 30 is closed and the computer 24 waits (passive systole) until the desired blood volume is ejected from the VAD (volume-limited mode) or the systolic time has elapsed (frequency-limited mode). Diastole begins by opening the cylinder venting valve 32. The compressed spring inside the bellows 28 then creates a vacuum for the blood-filling phase of the cycle (i.e., as the spring pushes the bellows outwards, the gas pressure in the driveline 34, connected to the VAD 12, decreases). Once the desired vacuum level is reached, as measured by the driveline pressure sensor 36, a vacuum regulating valve 38 (attached to the driveline 34) opens to let air into the VAD/inner piston space/driveline 34 insuring that the desired vacuum level is not exceeded. The computer 24 then waits for the desired blood volume to fill the VAD 12 (volume-limited mode) or until the diastolic time has elapsed (frequency-limited mode).

As noted above, the preferred driver means 10 utilizes controlled pressurized air for operating the VAD 12, as supplied to the console 14 from the pressurized air unit 16, and not a motor-driven pump or the like. The pressurized air unit 16 may be separate from the console 14, or attached thereto, e.g., as part of a mobile cart or the like (see FIGS. 3A–3C). The primary source of pressurized air is the pressurized air, oxygen or other gas supply 22 found in most hospital rooms, intensive care units, and operating rooms, which is connected to the unit 16 by the connector 20. The inlet pressure needs to be several times greater than the maximum systolic pressure desired, which is about 5 psi. Standard hospital oxygen and air supplies are regulated for fifty psi of pressure, which may be regulated by a regulator/alarm unit 40 positioned between the console 14 and the tanks 18 and supply line 22. The tanks 18a, 18b are provided as a backup in case the main supply line 22 is shut off, or where portability is needed. A selector valve 42, either computer-controlled or manual, is provided for selecting between the supply line 22 and tanks 18a, 18b. The regulator/alarm unit 40 may be configured to emit an alarm if the input pressure into the regulator/alarm unit 40, i.e., the line pressure or tank pressure, falls or drops below a certain level.

An inlet pressure sensor 44, in fluid communication with the console's pressurized air input line 46 and electrically connected to the computer 24, may be provided to issue a signal to the computer 24 to warn the user if the inlet pressure drops due to a supply failure.

The computer 24 can be of any appropriate design or configuration. In one exemplary embodiment, the computer 24 comprises a microcontroller or microprocessor 50 and associated standard components (RAM, I/O bus, etc.), a video controller 52 and display 54 operably connected to the microcontroller 50, a communications bus or port 56 (e.g., USB, Ethernet) for external access to the microcontroller, and an A/D and D/A converter 58 or other sensor/valve interface or control unit. The computer 24 also includes a speaker 60 for sounding alarms or the like.

Remaining components will be described with respect to the operation of the air-pressure powered driver 10.

Pneumatic ventricular assist devices work by applying air pressure to a bladder or sac effectively attached in parallel to a patient's heart. Specifically, when pressure is applied to the sac, blood in the sac is ejected. When the air pressure against the sac is reduced, the sac expands, causing blood to enter the sac. When appropriate directional valves are employed, this creates a pulsing or cyclical blood flow. According to the present invention, with reference to FIGS. 2A and 2B, this action is accomplished using computer-controlled valves, a source of pressurized air, and the pump cylinder with spring-loaded bellows or piston.

As shown in FIG. 2A, at the beginning of a cycle, the computer 24 opens the inlet pressure valve 30. This causes air to enter into the inlet side (i.e., intake chamber or input chamber) of the pump cylinder 26, which compresses the bellows and spring 28 (it should be noted that the intake chamber of the cylinder is sealed or separate from the outlet side or discharge chamber). Compressing the bellows 28 causes the pressure of the air/gas in the driveline 34 to increase, which in turn compresses the VAD bladder or sac 70, forcing blood out of the sac, through a VAD outlet valve 72, and into the patient's bloodstream.

Once the maximum desired pressure in the driveline 34 is achieved, as measured by the driveline pressure sensor 36, the inlet pressure valve 30 is closed and the computer 24 waits (passive systole) until the desired blood volume is ejected from the VAD 12 (volume-limited mode) or the systolic time has elapsed (frequency-limited mode). If the diastolic vacuum has not been established or is below the desired level (i.e., the driveline pressure is above the desired diastolic vacuum level), the computer 24 causes the vacuum regulating valve 38 to open momentarily to let a small amount of air escape the driveline 34 at the end of the systolic period.

As shown in FIG. 2B, diastole begins by opening the cylinder venting valve 32. The compressed spring inside the piston cylinder or bellows will then create a vacuum for the blood-filling phase of the cycle. Specifically, as pressurized air is let out of the cylinder 26, there is no longer enough pressure to counteract the spring in the bellows 28. The spring forces the bellows/piston 28 outwards, increasing the effective volume of the driveline 34 and reducing the air pressure therein. This causes the VAD bladder 70 to expand, drawing in blood through a one-way VAD inlet valve 74. Once the desired vacuum level is reached, as measured by the driveline pressure sensor 36, the vacuum regulating valve 38 is opened to let air into the driveline 34 insuring that the desired vacuum level is not exceeded. If the desired vacuum level is not reached then it will be adjusted for the next cycle by opening the vacuum regulating valve 38 as discussed above. The computer 24 then waits for the desired blood volume to fill the VAD (volume-limited mode) or until the diastolic time has elapsed (frequency-limited mode).

The blood volume in the VAD 12 can be measured directly by a sensor in the VAD chamber (not shown). The blood volume in the VAD blood sac need not be measured directly, however, allowing for a simpler VAD design, but can be indirectly calculated by the computer 24 (calibrated to the VAD and driveline deadspace) by using Boyle's law (assuming a constant temperature, $P1 \cdot V1 = P2 \cdot V2$) and measuring the displaced volume in the pump cylinder 26 and driveline and barometric pressures. The barometric pressure and displaced volume can be measured by having, respectively: (i) a barometric pressure sensor 80 operably attached to the computer 24; and (ii) a distance sensor 82 (LED, other optical sensor, or the like) in the pump cylinder 26 and operably connected to the computer 24, that measures the distance from one end of the pump cylinder to the bellows (or another appropriate measurement).

A safety pressure relief valve 84 is attached to the driveline 34 to insure that maximum VAD/driveline pressure (e.g., 5 psi) is never exceeded, which could lead to air leaks in the VAD 12.

Periodically or at user selected times, the driver 10 has the capability of venting the driveline 34 to prevent excess condensation and remove fouled air. This is accomplished at the end of the diastolic period by opening a driveline venting valve 86, positioned between the driveline 34 and the pressurized air input line 46, for a short time.

The VAD/inner-cylinder/driveline space 34 is pressurized with fresh air. Excess pressure is vented by the pressure relief valve 84. Then the vacuum regulating valve 38 is opened to vent the system.

The computer 24 is an electronic controllinf means for regulating maximum systolic ventricular pressure and maximum from a patient's heart, through the amount of gas selectively supplied to the pump's intake and exhaust chambers, wherein the computer 24 has the capability of controlling the entire process (mentioned in the paragraphs above) according to user selectable or manufacturer's preset parameters such as desired stroke volume, rate, VAD output, systolic to diastolic ratio, maximum diastolic volume, minimum systolic volume, maximum systolic pressure, and/or maximum diastolic vacuum. The computer, through its sensors, also has self diagnostic capabilities and can trigger warnings and alarms to the user. Finally, the computer may also have the capability of storing or relaying the operational status and performance of the driver to remote locations (nurses' station, doctor's office) via network or wireless communications 56.

Although the VAD pumping action is primarily effectuated using pressurized air, the computer, valves, and sensors are electrically powered, via a standard power supply (attached to a wall outlet), generator, battery power system, or the like (not shown).

Silencers or mufflers 88 may be attached to the outputs of the valves 32, 38, for minimizing noise as pressurized air is periodically let out of the driver's air lines.

An emergency foot pump or bellows 90 may be operably attached to the driveline 34, via a manual selector valve 92 and/or connector 94. In an emergency (i.e., complete loss of pressurized air and/or electrical power), the foot bellows 90 are pumped manually, causing a variable pressure to be applied to the VAD 12. Preferably, the air volume displaced by the bellows 90 is configured to generally match the displacement volume required for operating the VAD pumping sac 70.

Figure 3A:
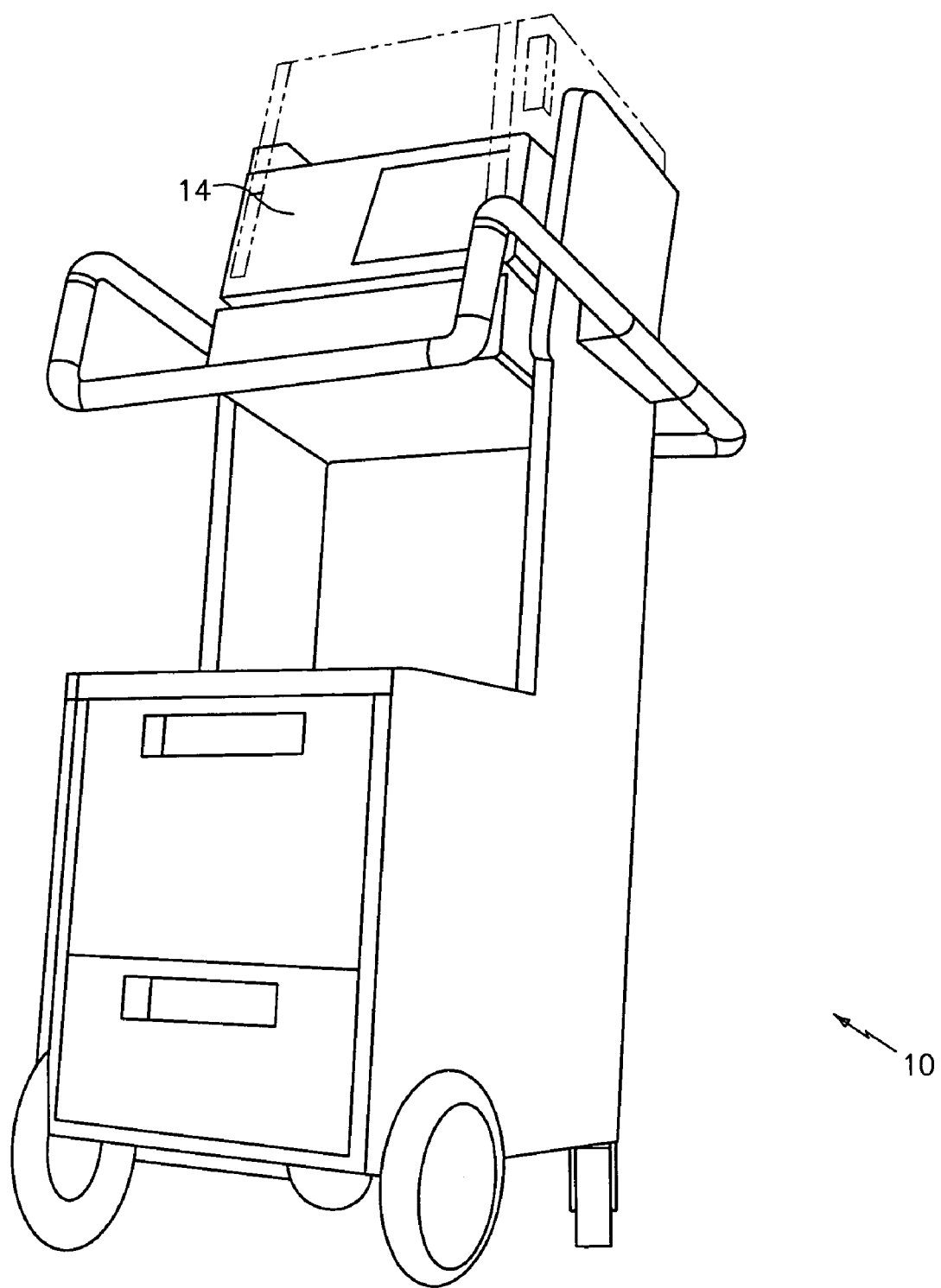
FIGS. 3A–3C are various views of the air-pressure powered driver as implemented as a wheeled, portable cart.
Figure 3B:
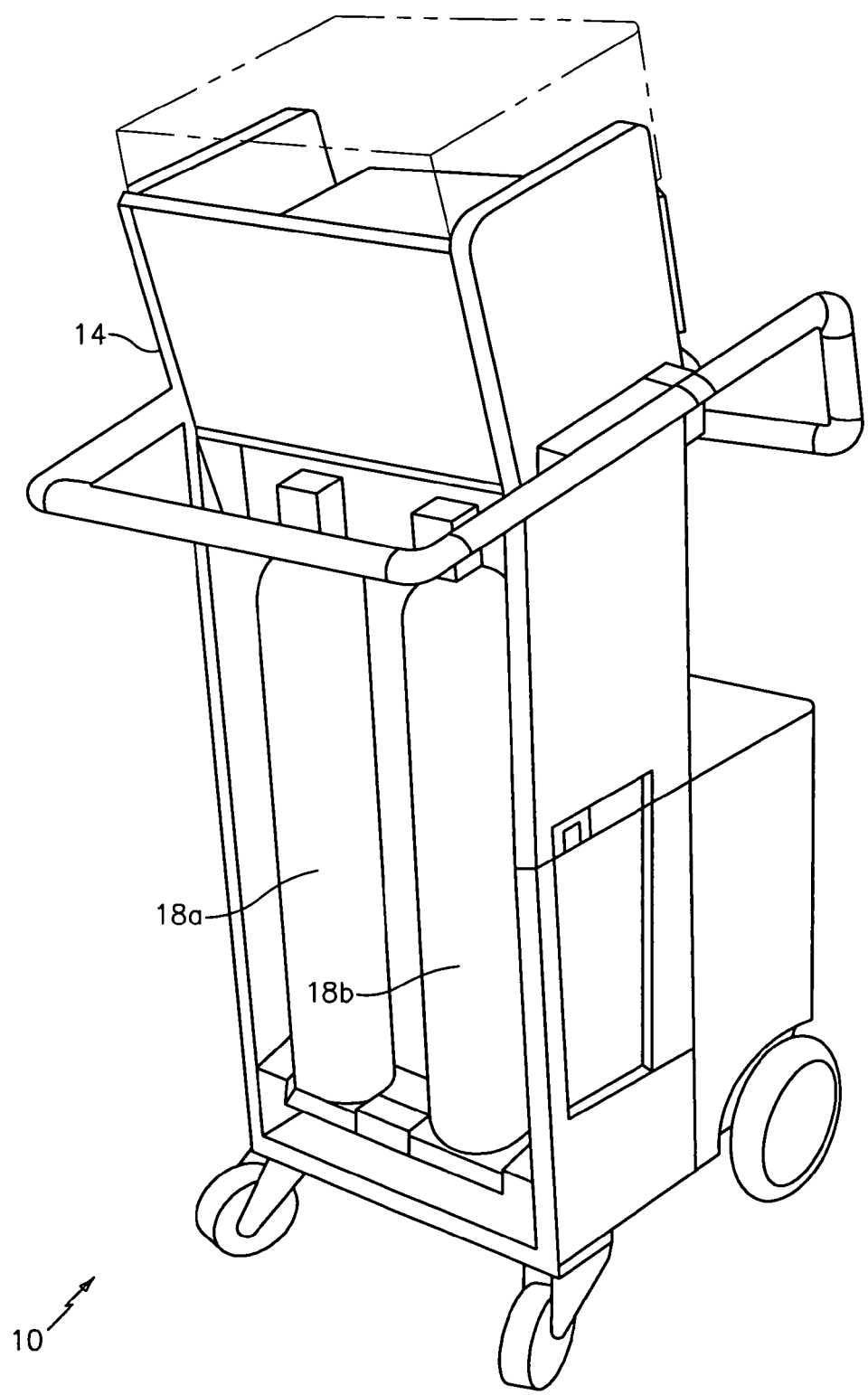
Figure 3C:
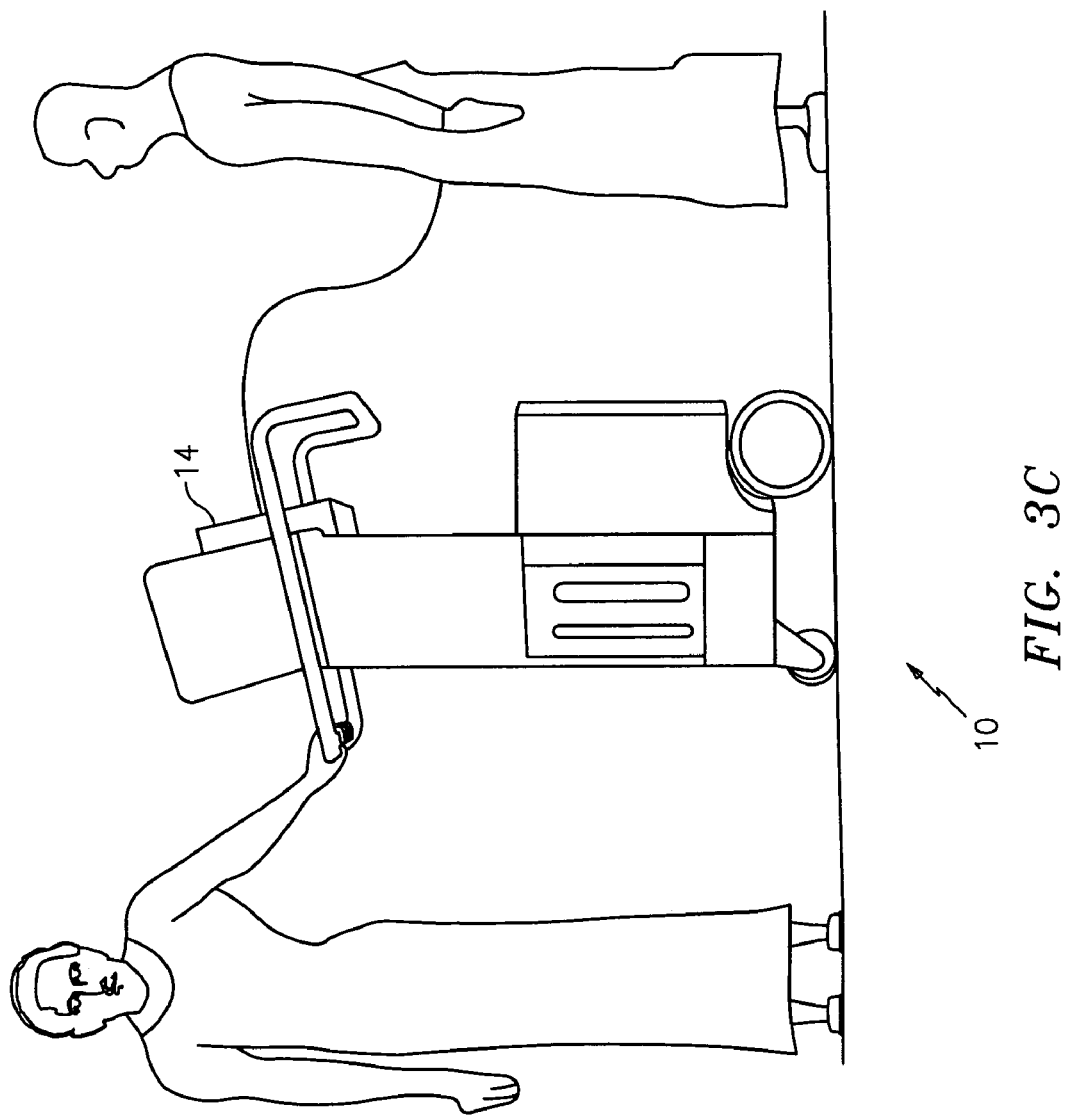

FIGS. 3A–3C show how the air-pressure powered driver 10 can be implemented as a portable cart.

Although the air-pressure powered driver has been described as having separate air inlet and pump venting valves 30, 32, respectively, a unitary air distribution device could be used instead, i.e., a computer-controlled device with three states: (i) "closed;" (ii) open to ambient (possibly through a muffler); and (iii) open to air input line 46. This is also the case for the valves 38, 84, 86 on the driveline 34. Thus, the term "air distribution device," as used herein, refers both to: stand-alone, discreet valves; multi-state valves; or a combination of the two.

Although the air-pressure powered driver has been illustrated as having a spring-loaded bellows or piston in the pump, a different biasing mechanism other than a spring could be used instead (polymer members, motor units, constructing the bellows out of a deformable material with a material memory, etc.). Accordingly, the term "biased air movement member" incorporates any bellows, pistons, or the like biased with a spring or other suitable device.

Since certain changes may be made in the above-described air-pressure powered driver for pneumatic ventricular assist devices, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. An apparatus comprising:
   a. a source of pressurized air;
   b. a pump cylinder connected in fluid communication to the pressurized air source by an air input line, wherein the pump cylinder comprises: an interior space; and a sealed, biased air movement member positioned in the interior space and dividing the interior of the pump cylinder into an input chamber and a discharge chamber;
   c. a pneumatic ventricular assistance device connected in fluid communication with the discharge chamber by a driveline, wherein the pneumatic ventricular assistance device comprises a sac that is selectively expandable and collapsible in response to air pressure emanating from the pump cylinder's discharge chamber;
   d. a first air distribution device in fluid communication with the air input line and the input chamber, wherein the first air distribution device can be electrically controlled to connect the input chamber to the air input line and to ambient atmosphere;
   e. a second air distribution device in fluid communication with the driveline and the air input line, wherein the second air distribution device can be electrically controlled to connect the driveline, and the pump cylinder to the ambient atmosphere; and
   f. electronic controlling means for regulating maximum systolic ventricular pressure and maximum diastolic vacuum from a patient's heart, through the amount of air selectively supplied to the pump's inlet and discharge chambers, without the need for an electric motor, wherein the controlling means comprises an electronic controller electrically connected to the first and second air distribution devices, wherein the electronic controller is configured: (i) to cause the first air distribution device to connect the input chamber to the air input line, thereby compressing the biased air movement member and causing a pressure level in the driveline to increase for driving the ventricular assist device during systole; (ii) to cause the first air distribution device to connect the input chamber to the ambient atmosphere, thereby reducing pressure against the biased air movement member and allowing the biased air movement member to move back to a non-compressed state, wherein the driveline pressure level decreases for driving the ventricular assist device during diastole; and (iii) to cause the second air distribution device to connect the driveline to the ambient atmosphere, for purposes of letting air into the driveline, when the driveline pressure level falls below a desired vacuum level for diastolic operation of the ventricular assist device.

2. The apparatus of claim 1 wherein the second air distribution device is further configured for being electrically controlled to connect the driveline to the air input line; and the electronic controller is configured to vent the driveline after diastole by causing the second air distribution device to open the driveline, and the pump cylinder, first to the air input line and then to the ambient atmosphere.

3. The apparatus of claim 2 wherein the second air distribution device comprises: a vacuum regulating valve in fluid communication with the driveline and the ambient atmosphere; and a driveline venting valve in fluid communication with the driveline, pump cylinder, and the air input line.

4. The apparatus of claim 1 wherein the first air distribution device comprises: an inlet pressure valve in fluid communication with the air input line and the pump cylinder input chamber; and a cylinder venting valve in fluid communication with the input chamber and the ambient atmosphere.

5. The apparatus of claim 1 further comprising a safety pressure relief valve in fluid communication with the driveline for venting air from the pump cylinder driveline when the driveline pressure exceeds a maximum ventricular assist device pressure.

6. The apparatus of claim 1 further comprising an inlet pressure sensor in fluid communication with the air input line for detecting a pressure level in the air input line, wherein the inlet pressure sensor is electrically connected to the electronic controller for alerting a user when the pressure level in the air input line falls below a pre-selected operational pressure level.

7. The apparatus of claim 1 further comprising sensors operably connected to the pump cylinder input chamber and to the driveline, and electrically connected to the electronic controller, for measuring pressure levels in the pump cylinder input and pump cylinder driveline.

8. The apparatus of claim 1 further comprising a pressurized air unit operably connected to the air input line, wherein the pressurized air unit comprises: at least one backup tank of pressurized air; and an air input connector configured for attachment to a facility-wide pressurized air line.

9. The apparatus of claim 8 further comprising a portable, wheeled cart, wherein the wheeled cart houses the electronic controller, the first and second air distribution devices, the pump cylinder, the air input line, and the pressurized air unit.

10. The apparatus of claim 1 further comprising a portable, wheeled cart, wherein the wheeled cart houses the electronic controller, the first and second air distribution devices, the pump cylinder, and the air input line.

11. The apparatus of claim 1 wherein the biased air movement member is a spring-loaded bellows.

12. An apparatus comprising:
  a. a source of pressurized gas;
  b. a pump connected in fluid communication with the pressurized gas source, wherein the pump comprises: a housing; and a biased air-movement member inside the housing that divides the housing into an intake chamber and a discharge chamber, wherein the discharge chamber is connected to a tubular outlet driveline;
  c. a pneumatic ventricular assistance device connected in fluid communication with the discharge chamber by the driveline, wherein the pneumatic ventricular assistance device comprises a sac that is selectively expandable and collapsible in response to gas pressure emanating from the pump's exhaust chamber;
  d. an inlet valve in fluid communication with the source of pressurized gas and the pump intake chamber, wherein the inlet valve is electrically controllable to connect the source of pressurized gas to the pump intake chamber;
  e. a pump venting valve in fluid communication with the pump housing inlet and ambient atmosphere, wherein the pump venting valve is electrically controllable to expose the pump intake chamber to ambient atmosphere;
  f. a vacuum regulating valve in fluid communication with the outlet driveline and ambient atmosphere, wherein the vaccum regulating valve is electrically controllable to expose the outlet driveline to the ambient atmosphere; and
  g. electronic controlling means for regulating maximum systolic ventricular pressure and maximum diastolic vacuum from a patient's heart, through the amount of gas selectively supplied to the pump's intake and discharge chambers, wherein the inlet valve and pump venting valve, wherein the computer is configured to periodically: (i) open the inlet valve to compress the biased air-movement member inside the pump housing until a desired maximum pressure in the outlet driveline is achieved for systolic operation of the ventricular assist device; (ii) close the inlet valve for passive systolic operation of the ventricular assist device; (iii) open the pump venting valve to decompress the biased gas-movement member for diastolic operation of the ventricular assist device; and (iv) open the vacuum regulating valve to allow air from the ambient atmosphere into the outlet driveline if the output driveline pressure falls below a desired minimum pressure in the outlet driveline for diastolic operation.

13. The apparatus of claim 12 further comprising a driveline venting valve in fluid communication with the outlet driveline and the source of pressurized gas, wherein the electronic controller is configured to vent the outlet driveline after diastole by first opening the driveline venting valve and then opening the vacuum regulating valve.

14. A gas powered driver for operating a pneumatic ventricular assist device comprising:
  a. a source of pressurized gas;
  b. a pump connected in fluid communication with the pressurized gas source, wherein the pump comprises: a housing; and a biased air-movement member inside the housing and dividing the housing into an inlet and an outlet driveline, said outlet driveline being configured for connection to a pneumatic ventricular assist device;
  c. an electrically-controllable inlet valve connected to the source of pressurized gas and to the pump housing inlet;
  d. an electrically-controllable pump venting valve connected to the pump housing inlet;
  e. an electrically-controllable vacuum regulating valve connected to the outlet driveline; and
  f. electronic controlling means for regulating maximum systolic ventricular pressure and maximum diastolic vacuum from a patient's heart, through the amount of gas selectively supplied to the pump's intake and exhaust chambers, wherein the controlling means comprises: a computer operably connected to the inlet valve and pump venting valve, wherein the computer is configured to periodically: (i) open the inlet valve to compress the biased air-movement member inside the pump housing until a desired maximum pressure in the driveline is achieved; (ii) close the inlet valve; (iii) once a desired time period has elapsed or a desired blood volume has been ejected from the ventricular assist device, to open the pump venting valve to decompress the biased air-movement member to reduce pressure in the pump outlet; and (iv) open the vacuum regulating valve if the pump outlet pressure falls below a desired minimum pressure in the pump outlet for diastolic operation of the ventricular assist device.

* * * * *

UNITED STATES PATENT AND TRADEMARK OFFICE
CERTIFICATE OF CORRECTION

PATENT NO.        : 7,074,176 B2
APPLICATION NO. : 10/846983
DATED             : July 11, 2006
INVENTOR(S)      : Emilio Sacristan It is certified that error appears in the above-identified patent and that said Letters Patent is hereby corrected as shown below:

Column 5, lines 7 - 16 of the Patent, combine lines 7 - 16 into 1 paragraph.

Column 5, line 17 of the Patent, change "controllinf" to --controlling--.

Column 5, line 19 of the Patent, after "maximun" insert --diastolic vacuum--.

Signed and Sealed this

Seventeenth Day of October, 2006

JON W. DUDAS
*Director of the United States Patent and Trademark Office*